US010072284B2

(12) United States Patent
Mertz, Jr. et al.

(10) Patent No.: US 10,072,284 B2
(45) Date of Patent: Sep. 11, 2018

(54) LYSIS BUFFER AND METHODS FOR EXTRACTION OF DNA FROM PLANT MATERIAL

(71) Applicant: MONSANTO TECHNOLOGY LLC, St. Louis, MO (US)

(72) Inventors: Thomas R. Mertz, Jr., Urbandale, IA (US); Saurabh Parikh, Bayside, NY (US); Julie Oermann, St. Louis, MO (US); Tracey Hodge, St. Charles, MO (US); Bryan Witherbee, St. Peters, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 14/406,849

(22) PCT Filed: Jun. 20, 2013

(86) PCT No.: PCT/US2013/046772
§ 371 (c)(1),
(2) Date: Dec. 10, 2014

(87) PCT Pub. No.: WO2014/018195
PCT Pub. Date: Jan. 30, 2014

(65) Prior Publication Data

US 2015/0167053 A1 Jun. 18, 2015

Related U.S. Application Data

(60) Provisional application No. 61/662,602, filed on Jun. 21, 2012.

(51) Int. Cl.
*C12Q 1/6806* (2018.01)

(52) U.S. Cl.
CPC .................................. *C12Q 1/6806* (2013.01)

(58) Field of Classification Search
None
See application file for complete search history.

(56) References Cited

U.S. PATENT DOCUMENTS 4,652,517 A * 3/1987 Scholl ...................... C12N 1/06 435/259
5,312,910 A 5/1994 Kishore et al.
5,346,999 A 9/1994 Catheart et al.
5,434,058 A * 7/1995 Davidson ............. C07K 14/775 435/199
5,500,363 A 3/1996 Comb et al.
5,518,885 A * 5/1996 Raziuddin .......... C07K 14/4705 435/6.14
5,776,717 A * 7/1998 Cao .................... C07K 14/4702 435/15
5,800,989 A * 9/1998 Linn .................... C12Q 1/6816 435/287.2
6,080,747 A * 6/2000 Uckun ................. A61K 31/517 514/266.1
6,127,155 A 10/2000 Gelfand et al.
6,245,519 B1 * 6/2001 Brentano ............. C12Q 1/6806 435/6.12
6,380,177 B1 * 4/2002 Erickson .............. A61K 31/661 514/141
6,921,817 B1 7/2005 Banerjee
7,074,600 B2 7/2006 Dean et al.
7,173,124 B2 2/2007 Deggerdal et al.
7,282,475 B2 10/2007 Porter et al.
7,931,920 B2 4/2011 Hildebrand
7,939,249 B2 5/2011 Parthasarathy et al.
7,985,540 B2 7/2011 Jensen et al.
7,989,614 B2 8/2011 Deggerdal et al.
2002/0081726 A1 * 6/2002 Russell ................ C12N 5/0068 435/366
2003/0022231 A1 1/2003 Wangh et al.
2003/0134797 A1 * 7/2003 Podolsky ............. C07K 14/575 435/69.1
2003/0228613 A1 * 12/2003 Bornarth ............. C12Q 1/6806 435/6.12
2003/0232749 A1 * 12/2003 Renzi ..................... A61K 31/00 514/438
2004/0180445 A1 9/2004 Domanico et al.
2005/0136477 A1 6/2005 Akhavan-Tafti
2005/0164260 A1 7/2005 Chen
2006/0024712 A1 2/2006 Baker et al.
2006/0063208 A1 * 3/2006 Woolf .................... G01N 33/74 435/7.2
2006/0199214 A1 9/2006 Jack et al.

(Continued)

FOREIGN PATENT DOCUMENTS

WO WO 2010048712 A1 * 5/2010 ......... A61K 31/4418

OTHER PUBLICATIONS

Sigma-Aldrich. Retrieved on Aug. 3, 2016 from the internet: http://www.sigmaaldrich.com/catalog/product/fluka/319503?lang=en®ion=US.*
Dellaporta et al., "A Plant DNA Minipreparation: Version II" Plant Molecular Biology Reporter, 1983, vol. 1, No. 4, pp. 19-21.
Clark et al., "Protocol: An improved high-throughput method for generating tissue samples in 96-well format for genotyping (Ice-Cap 2.0)", Plant Methods 2007, 3:8, 8 pages.
Shi et al., "Multiplex single nucleotide polymorphism (SNP) assay for detection of soybean mosaic virus resistance genes in soybean", Theor Appl Genet, 2011, vol. 122, pp. 445-457.

(Continued)

*Primary Examiner* — Joseph G Dauner
(74) *Attorney, Agent, or Firm* — Senniger Powers LLP; James E. Davis

(57) ABSTRACT

The present invention is generally directed to a lysis buffer for extraction of DNA from plant material and improved methods for extraction of DNA from plant material utilizing the novel lysis buffer. Advantageously, the lysis buffer of the present invention is suitable for use in connection with simpler analysis methods, while still providing suitable DNA yields and purities for analysis.

13 Claims, 5 Drawing Sheets

Specification includes a Sequence Listing.

(56) References Cited

U.S. PATENT DOCUMENTS

| | | | | |
|---|---|---|---|---|
| 2009/0012019 | A1 * | 1/2009 | Chang | C07K 14/705 514/44 R |
| 2009/0130687 | A1 | 5/2009 | Bendzko et al. | |
| 2009/0149646 | A1 | 6/2009 | Deggerdal et al. | |
| 2009/0227011 | A1 | 9/2009 | Chen | |
| 2010/0285578 | A1 | 11/2010 | Selden et al. | |
| 2010/0331534 | A1 | 12/2010 | Khan et al. | |
| 2011/0020883 | A1 * | 1/2011 | Roessler | C12N 9/16 435/134 |
| 2011/0159485 | A1 | 6/2011 | Stray et al. | |
| 2011/0177516 | A1 | 7/2011 | Himmelreich et al. | |

OTHER PUBLICATIONS

"Amplification of plant DNA with GenomiPhi DNA Amplification Kit", Amersham Biosciences, Application Note 63-0056-20, 6 pages.

International Search Report, PCT/US2013/46772, dated Oct. 29, 2013, 6 pages.

Written Opinion, PCT/US2013/46772, dated Oct. 29, 2013, 5 pages.

International Preliminary Report on Patentability, PCT/US2013/46772, dated Dec. 23, 2014, 7 pages.

Cane et al., "Expression and mechanistic analysis of a germacradienol synthase from Streptomyces coelicolor implicated in geosmin biosynthesis", PNAS, Feb. 18, 2003, vol. 100, No. 4, pp. 1547-1551.

Szekely et al., "EBNA-5, an Epstein-Barr virus-encoded nuclear antigen, binds to the retinoblastoma and p53 proteins", Proc Natl Acad Sci USA, Jun. 15, 1993; vol. 90, No. 12, pp. 5455-5459.

Kasem et al., "DNA Extraction from Plant Tissue", Plant genotyping II: SNP technology, Chapter 14, 2008, pp. 219-271.

Wittwer et al., "Magic in Solution: an Introduction and Brief History of PCR", PCR Troubleshooting and Optimization: The Essential Guide, 2011, Chapter 1, pp. 1-21.

Henry, R.J., "Plant DNA Extraction", Plant Genotyping: The DNA Fingerprinting of Plants, 2001, Chapter 16, pp. 239-250.

Erickson et al., "Integrated microfluidic devices", Analytica Chimica Acta, vol. 507, 2004, pp. 11-26.

Weising et al., DNA Fingerprinting in Plants: Principles, Methods, and Applications, 2005, Second Edition, 444 pages.

Karakousis et al., "A High-Throughput Plant DNA Extraction Method for Marker Analysis", Plant Molecular Biology Reporter, Mar. 2003, vol. 21, Issue 1, pp. 95a-95f.

Qiagen Buffers—OpenWetWare, 2012, 3 pages, <http://openwetware.org/wiki/Qiagen_Buffers>.

Hodkinson et al., "DNA banking for plant breeding, biotechnology and biodiversity evaluation", Journal of Plant Research, Jan. 2007, vol. 120, Issue 1, pp. 17-29.

Wang et al., "A simple method of preparing plant samples for PCR", Nucleic Acids Research, 1993, vol. 21, No. 17, pp. 4153-4154.

Nguyen et al., "Comparison of DNA extraction efficiencies using various methods for the detection of genetically modified organisms (GMOs)", International Food Research Journal, 2009, vol. 16, pp. 21-30.

Porebski, S., et al., "Modification of a CTAB DNA Extraction Protocol for Plants Containing High Polysaccharide and Polyphenol Components," Plant Molecular Biology Reporter, 1997, pp. 8-15, vol. 15, No. 1.

* cited by examiner

1 – (Adjacent + Flipped / Total) = Concordance

SEQUENCE LISTING

```
<160> NUMBER OF SEQ ID NOS: 4

<210> SEQ ID NO 1
<211> LENGTH: 635
<212> TYPE: DNA
<213> ORGANISM: Zea mays
<220> FEATURE:
<221> NAME/KEY: Unsure
<222> LOCATION: (1)..(635)
<223> OTHER INFORMATION: unsure at all n locations
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (151)..(151)
<223> OTHER INFORMATION: n is a, c, g, or t
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
<222> LOCATION: (463)..(463)
<223> OTHER INFORMATION: n is a, c, g, or t
<220> FEATURE:
<221> NAME/KEY: misc_feature
<222> LOCATION: (465)..(471)
<223> OTHER INFORMATION: n is a, c, g, or t
<220> FEATURE:
<221> NAME/KEY: misc_feature
<222> LOCATION: (475)..(476)
<223> OTHER INFORMATION: n is a, c, g, or t
<220> FEATURE:
<221> NAME/KEY: misc_feature
<222> LOCATION: (478)..(482)
<223> OTHER INFORMATION: n is a, c, g, or t
<220> FEATURE:
<221> NAME/KEY: misc_feature
<222> LOCATION: (520)..(522)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (544)..(566)
<223> OTHER INFORMATION: n is a, c, g, or t
<220> FEATURE:
<221> NAME/KEY: misc_feature
<222> LOCATION: (568)..(570)
<223> OTHER INFORMATION: n is a, c, g, or t
<220> FEATURE:
<221> NAME/KEY: misc_feature
<222> LOCATION: (580)..(609)
<223> OTHER INFORMATION: n is a, c, g, or t
<220> FEATURE:
<221> NAME/KEY: misc_feature
<222> LOCATION: (611)..(633)
<223> OTHER INFORMATION: n is a, c, g, or t

<400> SEQUENCE: 1

ataactacat ataatttcta ttgttatctt tngggggtac catgtgcact aacacatact     60

gcattcgtgg atctgtttat tatattgtgc aggttaagaa aaagttggtg aatctgggtc    120
```

```
atgcacagag gtacgtcgtg atttgctaat ntgtnatttt aagaaaaggg cagacccggt    180

atcgaaggct cccatgtgag tggggtttgg ggagagaaac cgaggcaagt cttcctccac    240

aaatgtggag aggctgcttc gaatcagcga ctggtgcctc agtgagacag ctctcaccac    300

cgcaccaggc gtgctcttcg tttactaatc tgctatttaa taaagcacaa tgaacagact    360

accatcttta tgttcaaatc gaaaatagtg aggaatcact tcatttgctg attttaagtt    420

cctggcctaa tctaaatgtt agttttttaa ggctttgaat tcnannnnnn nattnngnnn    480

nntctgaaaa atgtcatttt ttattcttat atggaagttn nnaaatatgc aaatatgacn    540

aacnnnnnnn nnnnnnnnnn nnnnnncnnn tatgatctan nnnnnnnnnn nnnnnnnnnn    600

nnnnnnnnnt nnnnnnnnnn nnnnnnnnnn nnntg                               635
```

<210> SEQ ID NO 2
<211> LENGTH: 635
<212> TYPE: DNA
<213> ORGANISM: Zea mays
<220> FEATURE:
<221> NAME/KEY: Unsure
<222> LOCATION: (1)..(635)
<223> OTHER INFORMATION: unsure at all n locations
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (151)..(151)
<223> OTHER INFORMATION: n is a, c, g, or t
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
<222> LOCATION: (463)..(463)
<223> OTHER INFORMATION: n is a, c, g, or t
<220> FEATURE:
<221> NAME/KEY: misc_feature
<222> LOCATION: (465)..(471)
<223> OTHER INFORMATION: n is a, c, g, or t
<220> FEATURE:
<221> NAME/KEY: misc_feature
<222> LOCATION: (475)..(476)
<223> OTHER INFORMATION: n is a, c, g, or t
<220> FEATURE:
<221> NAME/KEY: misc_feature
<222> LOCATION: (478)..(482)
<223> OTHER INFORMATION: n is a, c, g, or t
<220> FEATURE:
<221> NAME/KEY: misc_feature
<222> LOCATION: (520)..(522)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (544)..(566)
<223> OTHER INFORMATION: n is a, c, g, or t
<220> FEATURE:
<221> NAME/KEY: misc_feature
<222> LOCATION: (568)..(570)
<223> OTHER INFORMATION: n is a, c, g, or t
<220> FEATURE:
<221> NAME/KEY: misc_feature
<222> LOCATION: (580)..(609)
<223> OTHER INFORMATION: n is a, c, g, or t
<220> FEATURE:
<221> NAME/KEY: misc_feature
<222> LOCATION: (611)..(633)

<223> OTHER INFORMATION: n is a, c, g, or t

<400> SEQUENCE: 2

```
ataactacat ataatttcta ttgttatctt tnggggggtac catgtgcact aacacatact     60
gcattcgtgg atctgtttat tatattgtgc aggttaagaa aaagttggtg aatctgggtc    120
atgcacagag gtacgtcgtg atttgctaat ntgtnatttt aagaaaaggg cagacccggt    180
atcgaaggct cccatgtgag tggggtttgg ggagagaaac cgaggcaagt cttcctccac    240
aaatgtggag aggctgcttc gaatcagcga ctggtgcctc agtgagacag ctctcaccac    300
cgcaccaggc gtgctcttcg tttactaatc tgctatttaa taaagcacaa tgaacagact    360
accatcttta tgttcaaatc gaaaatagtg aggaatcact tcatttgctg attttaagtt    420
cctggcctaa tctaaatgtt agttttttaa ggctttgaat tcnannnnnn nattnngnnn    480
nntctgaaaa atgtcatttt ttattcttat atggaagttn nnaaatatgc aaatatgacn    540
aacnnnnnnn nnnnnnnnnn nnnnnncnnn tatgatctan nnnnnnnnnn nnnnnnnnnn    600
nnnnnnnnnt nnnnnnnnnn nnnnnnnnnn nnntg                              635
```

<210> SEQ ID NO 3
<211> LENGTH: 546
<212> TYPE: DNA
<213> ORGANISM: Zea mays

<400> SEQUENCE: 3

```
gtcgatccgt tccttcaaaa ttgattccaa tcggattgct ccctcaaagt tgctcttcaa     60
attctaggga ataaatgcta tagttggcgc acgcgcagtc gatatgggaa ttttgaccac    120
ccctcaactg cattggatgg tccggagcaa aaacaaaggt gtcatggctt ccgagtcaga    180
ttattttagg cagcttattg gatcgttcag gttattttct agtcattgtc ctgctgcttt    240
tagtctccca cgaactacta tagtgtcttt gatgatgagt ttctagcatc aaatttcacc    300
aggcgtatgt tggaattagt gccaaaaggt aaaggtgggg atgaggttgc caagaaactt    360
attgtcgatg gagcaaatgg cattggtggg gtgaagctcg aacaaataaa ggtggagctt    420
tcaggcatag atattagtgt gaggaattcg ggcaaggaag gagaagggat actaaatcac    480
atgtgtggcg cagactttgt tcaaaaggag cgagttactc cacatggatt taaccctgaa    540
gatgtt                                                               546
```

<210> SEQ ID NO 4
<211> LENGTH: 682
<212> TYPE: DNA
<213> ORGANISM: Zea mays

<400> SEQUENCE: 4

```
ctatggaagc tcccagtacg gtccaccact ctgtcaggtg agaagaagct taattatatt     60
gattaaatat aacaactaac tggagcaaga ctaaaggaaa taaaacatgt ttttttgtg    120
ggaaatcccc tacattttct aatttctact catgtaaaac tagctactgc aggttgttgt    180
caatgccatc acttgaattt agctagagag atttatttat ttatttattt cttaccagca    240
ctgtcgaacc tctggctgcc agggcgacag tgtcagcaca ggacaccgtc tgcggacatg    300
cttcctcgag tgcagctttg atctcgtcta tgacctcaaa ccccctaatg gaatccttgt    360
tggggatagc gtttttctcg ctcacgactt cctcagcgtc atccaaaaga accgacgcat    420
cgcagccctg cgatagtgcg attagtttca tcgcatgaac cacggccggg acaaaagaga    480
cgattgacca aatagagaac atgagaccgt agtgctgcta acctggacaa agcagtcatg    540
```

-continued

```
gaacaggagc ctgagaaggg aggcagctac ccgtggttcc ttcgcgatag ccttcttcag    600

tatgggcgcc accgtctcgt cagcttgcgg gcatgtcaac ctgtagtagt ctgtagaaag    660

acctgggatt ggagtacttc ca                                              682
```

LYSIS BUFFER AND METHODS FOR EXTRACTION OF DNA FROM PLANT MATERIAL

REFERENCE TO RELATED APPLICATIONS

This application is a U.S. national stage application of International Application No. PCT/US2013/046772, filed Jun. 20, 2013, and claims the benefit of U.S. Provisional Application Ser. No. 61/662,602, filed Jun. 21, 2012, the entire contents of which are incorporated herein by reference.

FIELD OF THE INVENTION

The present invention is generally directed to a lysis buffer for extraction of DNA from plant material and improved methods for extraction of DNA from plant material utilizing the novel lysis buffer. Advantageously, the lysis buffer of the present invention is suitable for use in connection with simpler analysis methods, while still providing suitable DNA yields and purities for analysis. In particular, the lysis buffer and methods of the present invention are suitable for DNA analysis methods that provide reduced cost per sample analyzed. Along with such advantages, the lysis buffer of the present invention is effective for extraction of DNA from a wide variety of plants and crops (e.g., corn, soy, and wheat) and a wide variety of types of plant material (e.g., whole seed samples, chipped seed samples, leaf samples, and bulk plant material samples). In addition, DNA extracted utilizing the current lysis buffer and/or the methods detailed herein are suitable for use in a variety of applications including, for example, single nucleotide polymorphism (SNP) studies and marker-assisted breeding studies.

BACKGROUND OF THE INVENTION

The extraction of DNA from plants is the starting point for genotype analysis. Generally, the approach to recovery of DNA from plants is determined by the species, the type of tissue sample available, and the desired DNA analysis. The quality and quantity of DNA required for the post extraction analytical techniques may dictate the protocol used for the DNA isolation.

Common elements of DNA isolation and purification methods include disruption of plant tissues and cells, DNA release into the extraction buffer, and purification of the DNA molecule from other cell ingredients such as proteins, membranes, RNA, polysaccharides, and polyphenols. One difficulty in isolation of DNA from plant cells is the presence of a cell wall that must be degraded physically or enzymatically in order to isolate the DNA. The method used to lyse the cell must be sufficient to disrupt the cell membrane while minimizing the shearing of the nucleic acid into shorter fragments. Furthermore, some plant species contain high levels of starches or phenols that can complicate DNA isolation.

Many commercial products designed for DNA recovery and purification exist. In commercial kits, a common lysis buffer contains tris(hydroxymethyl)aminomethane, ethylenediaminetetraacetic acid (EDTA), sodium chloride, and sodium dodecyl sulfate. Many commercial kits also contain an enzyme such as Proteinase K in addition to the lysis buffer. Unfortunately, residual amounts of impurities in the recovered DNA can inhibit or reduce the efficiency of downstream applications, such as PCR amplification. Also, the routine use of commercial kits for large scale marker assisted selection programs is expensive. Certain conventional lysis buffers are typically utilized in processing methods that include numerous steps (e.g., filtration of sample prior to recovery of a sample for analysis). Each step of the processing increases the cost per sample analyzed. Accordingly, lysis buffers and analysis methods that are amenable to eliminating steps are desired. Moreover, as automated methods for analysis are developed and a greater volume of samples are desired to be tested, simpler processing methods that would reduce the cost per sample are even further desired.

Other issues have also been encountered in connection with conventional lysis buffers. Because of the considerable variation in biochemical composition across plant species and tissues, difficulties have been encountered in supplying a single buffer composition and recovery/isolation protocol suitable for use across a wide variety of plant types and types of plant materials.

Thus, there exists a need in the art for a lysis buffer that is suitable for use in more economical processing methods (i.e., providing a reduced cost per sample analyzed). Additionally or alternatively, there exists a need in the art for a lysis buffer suitable for extraction of DNA across a wide variety of crops and plant species and a wide variety of types of plant material.

SUMMARY OF THE INVENTION

Briefly, therefore, the present invention is directed to an improved lysis buffer suitable for use in more economical sample analysis. The present invention is further directed to an improved lysis buffer effective for extraction of DNA from a wide variety of crops and plants and from a wide variety of plant materials. In this manner, the lysis buffer of the present invention is universal. The present invention is further directed to improved methods for extraction of DNA from plant material that are more efficient than conventional methods (e.g., reduce the cost per sample analyzed), provide DNA at higher yields and/or purity than conventional methods, are suitable for extraction of DNA from relatively small samples of plant material, and/or that are suitable for use in automated methods for extraction of DNA from plant material.

In various embodiments, the present invention is directed to a cell lysis buffer composition comprising: (a) a buffering component selected from the group consisting of tris(hydroxymethyl)aminomethane (Tris), 4-(2-hydroxyethyl)-1-piperazineethanesulfonic acid (HEPES), 3-(N-morpholino) propanesulfonic acid (MOPS), sodium dihydrogen phosphate ($NaH_2PO_4$), disodium hydrogen phosphate ($Na_2HPO_4$), and combinations thereof; (b) a mineral salt selected from the group consisting of sodium chloride (NaCl), potassium chloride (KCl), diammonium sulfate ($NH_4SO_4$), and combinations thereof; (c) a metal chelating agent selected from the group consisting of ethylenediaminetetraacetic acid (EDTA), ethylene glycol tetraacetic acid (EGTA), and combinations thereof; and (d) a surfactant selected from the group consisting of sodium dodecyl sulfate (SDS), nonyl phenoxypolyoxylethanol (NP-40), polyethylene glycol p-(1,1,3,3-tetramethylbutyl)-phenyl ether (triton-X), polyoxyethylene (20) sorbitan monooleate (Tween-20), and combinations thereof.

In various such embodiments, the composition further comprising one or more of the following components: (A) an alkali metal hydroxide selected from the group consisting of sodium hydroxide, potassium hydroxide, and combinations thereof; and/or (B) a precipitant selected from the group consisting of glycerol, dimethyl sulfoxide (DMSO), acetonitrile (ACN), bovine serum albumin (BSA), proteinase K, acetate salts, and combinations thereof; and/or (C) a water-soluble polymer comprising polyvinylpyrrolidone.

In still further such embodiments, the composition further comprises sodium hydroxide at a concentration of from about 100 mM to about 150 mM or about 125 mM.

In even further embodiments, the surfactant constitutes at least 0.5 wt % of the composition.

The present invention is also directed to a cell lysis buffer composition, the composition comprising a buffering component, a mineral salt, a metal chelating agent and a surfactant, the composition further comprising glycerol as a precipitant.

The present invention is still further directed to a method for the isolation of nucleic acid from plant material, the method comprising: (i) combining the plant material and a lysis buffer composition as defined in any of the preceding claims, thereby forming a plant material/lysis buffer mixture; (ii) agitating the plant material/lysis buffer mixture, thereby lysing the plant material and forming a lysed plant material mixture; (iii) separating the lysed plant material mixture into a mixture comprising a solids fraction comprising plant material and a supernatant comprising nucleic acid; and (iv) recovering the nucleic acid supernatant from the lysed plant material mixture.

Other objects and features will be in part apparent and in part pointed out hereinafter.

DETAILED DESCRIPTION OF THE PREFERRED EMBODIMENTS

Figure 1:
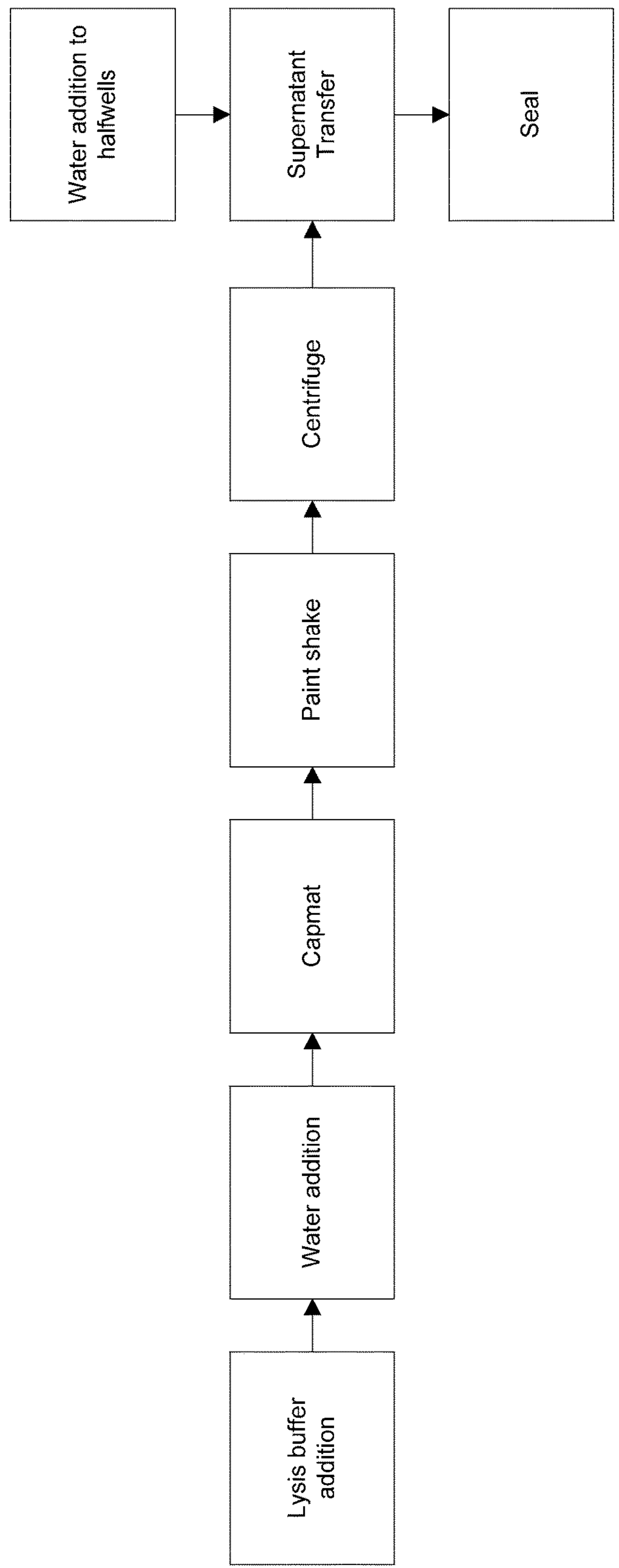
FIG. 1 displays an analysis protocol followed as described in Example 1.

The present invention provides an improved cell lysis buffer composition for use in connection with lysis of plant material and recovery of DNA. As detailed below, the lysis buffer, or buffer composition includes one or more components and/or a combination of components not found in conventional lysis buffers. Advantageously, the lysis buffer of the present invention has been observed to provide various advantages in connection with lysis of plant material.

One advantage of the present lysis buffer is its suitability for use in connection with simpler processing methods, including processing methods that eliminate operations, or steps typically used in analysis protocols utilizing conventional buffers. For example, the present lysis buffer may be utilized in extraction methods that do not require filtration of the lysate or an ethanol precipitation step, which may typically be used in connection with recovery of DNA with conventional lysis buffers, thereby removing a step from the recovery/isolation process and reducing material and processing requirements and, thus, likewise reducing the cost per sample analyzed. Since the lysis buffer is suitable for use in connection with more efficient processing, the methods in which it is utilized are more cost-effective and/or provide more samples for analysis over a certain period time than would be provided by a conventional lysis buffer.

In addition, since the lysis buffer efficiently provides a large number of samples, it is suitable for use in connection with both manual and automated protocols (e.g., high throughput analysis methods).

In addition, the present lysis buffer is suitable for use with plant material derived from various crops (e.g., corn, soy, and wheat) and for use with various types of plant material (e.g., leaf material and seed chips). In this manner, the lysis buffer may generally be referred to as universal. In addition, the lysis buffer provides for recovery of nucleic acid (i.e., DNA) that is suitable for use with essentially any analysis method known in the art. For example, the lysis buffer provides samples having suitable purities and/or also suitable yields of DNA that render it useful in connection with essentially any analysis method known in the art.

A further advantage of the present lysis buffer is its suitability for use in connection with chipped seed samples. In particular, the lysis buffer is suitable for use with chipped seed samples prepared by automated seed chipping methods. More particularly, the lysis buffer of the present invention is currently believed to be suitable for use in connection with advanced, automated seed chipping technology by virtue of providing sufficient yields and purities of samples from relatively small chipped seed samples typically utilized in automated seed chipping protocols.

Furthermore, since the lysis buffer provides DNA samples of high purity, significantly less downstream clean-up after recovery of DNA and prior to analysis is required, and in certain instances may be avoided altogether.

I. Lysis Buffer Composition

Buffering Component

Generally, the lysis buffer of the present invention includes a buffering component to provide a suitable chemical environment for extraction and recovery of DNA analysis, including a chemical environment that is suitable for the activity and stability of the DNA polymerase.

The buffering component may be selected from those generally known in the art. Typically, however, the buffering component is selected from the group consisting of tris(hydroxymethyl)aminomethane (Tris), 4-(2-hydroxyethyl)-1-piperazineethanesulfonic acid (HEPES), 3-(N-morpholino)propanesulfonic acid, (MOPS), Sodium dihydrogen phosphate ($NaH_2PO_4$), disodium hydrogen phosphate ($Na_2HPO_4$) and combinations thereof. In various preferred embodiments, the buffering component comprises Tris.

Generally, the buffering component is present at a concentration of at least about 100 mm or at least about 150 mM. Typically, the buffering component is present at a concentration of from about 100 to about 300 mM or from about 150 to about 250 mM.

Salt

A further component of the present lysis buffer is a salt, typically a mineral salt. The salt provides break-down of cell components to aid in providing DNA for extraction and recovery. The selection of the salt is not narrowly critical and generally any suitable salt known in the art may be utilized. Typically, the salt is a mineral salt selected from the group consisting of sodium chloride (NaCl), potassium chloride (KCl), diammonium sulfate ($NH_4SO_4$), and combinations thereof. In various preferred embodiments, the mineral salt comprises sodium chloride.

Generally, the (mineral) salt is present at a concentration of at least at about 100 mM, at least about 150 mM, or at least about 200 mM. Typically, the (mineral) salt is present at a concentration of from about 150 to about 350 mM or from about 200 to about 300 mM.

Chelating Agent

A further component of the extraction buffer of the present invention is a metal chelating agent for the purpose of binding with metal ions present in the extraction buffer that could degrade DNA and, therefore, reduce yields. The selection of the metal chelating agent is not narrowly critical and generally may be selected from those known in the art for use in lysis buffers. Typically, however, the metal chelating agent is selected from the group consisting of ethylenediaminetetraacetic acid (EDTA), ethylene glycol tetraacetic acid (EGTA), and combinations thereof. In various preferred embodiments, the chelating agent comprises EDTA.

Generally, the chelating agent is present at a concentration of at least about 10 mM or at least about 15 mM (e.g., about 25 mM). Typically, the chelating agent is present at a concentration of from about 10 to about 50 mM or from about 15 to about 40 mM.

In accordance with the present invention, as detailed below, various additional components and/or increased proportions of buffer components are utilized to provide the various advantages highlighted above.

Surfactant

Various conventional lysis buffers include a surfactant, or detergent component (often referred to as an ionic detergent). The surfactant/detergent is known to disrupt cell walls to release DNA, but also in the case of polysaccharide-rich plant tissues is known to separate polysaccharides from the extracted DNA. Suitable surfactants/detergents include those generally known in the art. Typically, however, the surfactant is selected from the group consisting of sodium dodecyl sulfate (SDS), nonyl phenoxypolyoxylethanol (NP-40), polyethylene glycol p-(1,1,3,3-tetramethylbutyl)-phenyl ether (triton-X), polyoxyethylene (20) sorbitan monooleate (Tween-20), sarkosyl, CTab, and combinations thereof. In various preferred embodiments, the surfactant comprises SDS.

Buffers known in the art may include a surfactant such as SDS. However, in accordance with the present invention it has been discovered that increasing the proportion of SDS above concentrations known in the art may provide various advantages. In various embodiments, SDS constitutes at least 0.5 wt % of the composition, or at least about 0.75 wt % of the composition. In various other embodiments, SDS constitutes between 0.5 wt % and about 1.5 wt %, from about 0.75 wt % to about 1.25 wt %, or about 1 wt %. In particular, it has been observed that increasing the proportion of SDS contributes to improved performance, at least in part, by virtue of providing increased disrupting of cell walls and release of DNA.

Precipitant

In accordance with the present invention, the lysis buffer typically includes a precipitant. Generally, the cell lysis provides a lysed plant material mixture that comprises a supernatant comprising DNA and a solids fraction. The precipitant contributes to formation of a solids portion (i.e., a "pellet") in the lysed plant material mixture that includes a significant fraction of impurities, cellular components, etc. and thereby provides a relatively pure DNA sample in the supernatant. Thus, the presence of the precipitant contributes to providing a relatively pure DNA sample. For example, the presence of the precipitant (e.g., glycerol) is currently believed to contribute to sufficient impurity removal such that a filtration step is not required prior to sample recovery. The presence of the precipitant may also avoid the need for cleaning of the DNA sample prior to subsequent analysis (e.g., PCR), or at least reduce the degree of cleaning required to prepare the sample for analysis.

In various embodiments, the precipitant is selected from the group consisting of glycerol, dimethyl sulfoxide (DMSO), acetonitrile (ACN), bovine serum albumin (BSA), proteinase K, acetate salts, and combinations thereof. Suitable acetate salts include, for example, sodium acetate (NaAc) and potassium acetate (KAc). In various embodiments, the bulking agent comprises glycerol.

The precipitant is generally present at a concentration (v/v) of at least about 0.5 wt % of the composition, or at least about 0.75 wt % of the composition. Typically, the precipitant is present at a concentration (v/v) of from about 0.5% to about 1.5%, from about 0.75% to about 1.25%, or about 1%.

In various preferred embodiments, the precipitant is glycerol. For example, the presence of glycerol has been observed to provide extremely pure samples of DNA for analysis. In this regard, glycerol is believed to act as a stabilizing agent, supporting pelleting of sample debris, thereby contributing to a cleaner lysate for DNA analysis. One result observed in connection with the purer sample is improved "clustering" of markers identified in DNA analysis. This result is demonstrated, for example, in Examples 1 and 2.

As noted above, in various embodiments the cell lysis buffer includes a higher proportion of surfactant than included in many conventional lysis buffers. For example, in various embodiments the lysis buffer includes greater than 0.5 wt. % of a surfactant (e.g., SDS). This greater proportion of surfactant provides greater disruption of cell walls. It is currently believed that the higher proportion of surfactant provides advantages on its own in this regard. And, as noted above, the presence of the precipitant/glycerol component likewise provides advantages in its own regard. It is currently further believed that the combination of the higher proportion of surfactant and glycerol as a precipitant provides advantageous cell wall disruption while also providing a DNA sample exhibiting suitable DNA purity and yield. That is, the presence of glycerol as a precipitant provides suitable formation of the "pellet" accounting for the greater disruption of cell walls and potential increased release of impurities provided by the greater proportion of surfactant.

Polymer

A further component of the lysis buffer of the present invention is a polymeric component, which serves to bind with contaminants present in the lysed plant material mixture and thereby have these components present in the solids fraction (i.e., pellet) of the lysed plant material mixture. Contaminants controlled and/or removed by the polymer include polyphenols and polysaccharides. The presence of these contaminants in DNA extraction often renders the sample viscous and results in low DNA yields and/or quality unsatisfactory for downstream analysis. Contaminant control by the polymer provides a relatively pure DNA sample and reduces the need for downstream clean-up prior to subsequent analysis (e.g., restriction endonuclease digestion, polymerase chain reaction (PCR), genotyping and sequencing).

Typically, the lysis buffer comprises a polymer comprising polyvinylpyrrolidone (PVP). In various preferred embodiments, the water-soluble polymer is PVP-10 (commercially available from SIGMA-ALDRICH).

Generally, the polymer is present at a concentration (w/v) of at least about 0.5 wt % of the composition, or at least about 0.75 wt % of the composition. Typically, the polymer is present at a concentration of from about 0.5% to about 1.5%, from about 0.75% to about 1.25%, or about 1%.

II. Plant Material

Advantageously, the present lysis buffer is suitable for use in connection with plant material from virtually any crop and also any type of plant material. In this manner, the lysis buffer is a universal buffer.

For example, the lysis buffer is suitable for use in connection with crop plants such as corn, soy, wheat, sugarcane, cotton, melon, cucumber, pepper, and tomato. In various embodiments, the crop plant is corn, soy, or wheat. In certain embodiments, the crop plant is corn. In certain other embodiments, the crop plant is soy. In particular, the lysis buffer is suitable for use with genetically modified plants.

With respect to the type of plant material, the lysis buffer is suitable for use with whole seed samples, chip samples, leaf samples. Whole seed samples are provided by grinding a single seed. The lysis buffer is also suitable for use in connection with bulk samples provided by combining multiple (e.g., more than two) whole seed samples or multiple leaf samples. Bulk samples may be utilized for purposes of assaying for purity across a group of samples or plants. Bulk samples are often provided by combining samples from at least 5, at least 10, or at least 15 seeds. In accordance with these and other bulk samples, typically up to 50 seeds are utilized.

In various preferred embodiments, the plant material is seed chip prepared by manual seed chipping or automated seed chipping. In particular, in various such embodiments the plant material is seed chip prepared by automated seed chipping. Advances in seed chipping technology are often directed to providing smaller seed chip samples, thereby causing less damage to the seed material. The effectiveness of the present lysis buffer renders it suitable for DNA separation and recovery from relatively small seed chip samples. Accordingly, the present lysis buffer is suitable for us with seed chip samples provided by current seed chipping technology and is also currently believed to be suitable for use with even smaller seed chip samples that will be provided by advances in seed chipping technology. More particularly in various preferred embodiments, the present lysis buffer is suitable for use in connection with recovery of DNA from seed chip samples and analysis of the thus recovered DNA my microfluidic PCR analysis.

III. Nucleic Acid Recovery

Recovery of DNA utilizing the lysis buffer of the present invention generally proceeds by combining the lysis buffer with the targeted plant material, agitating the mixture of the plant material and lysis buffer to provide a mixture including a supernatant including DNA to be recovered and a solids fraction, and recovering the DNA-containing supernatant.

Combining the lysis buffer and plant material forms a plant material/lysis buffer mixture. Typically, formation of the plant material/lysis buffer mixture includes dilution of the lysis buffer with an aqueous medium (e.g., deionized water).

Generally, an aqueous medium is combined with the lysis buffer at a volumetric ratio (aqueous medium:lysis buffer) of at least about 5:1 or at least about 10:1 for dilution. For example, typically an aqueous medium is combined with the lysis buffer mixture at a volumetric ratio (aqueous medium: lysis buffer) of from about 5:1 to about 20:1, of from about 10:1 to about 20:1, or about 15:1.

After the plant material and lysis buffer have been combined, the mixture is treated to provide breakdown of plant cell walls and release of DNA. Typically, this treatment includes agitation of the plant material/lysis buffer mixture, which generally includes placing samples of the mixture into a suitable container (e.g., a multi-well plate) and shaking of the samples.

In various embodiments, the agitation for breakdown of cell walls and release of DNA includes contacting the plant material with particulate matter for facilitating breakdown of the cell walls. In particular, this contact generally includes placing suitable particulate matter in each well of the multi-well plate so that the particulate matter and plant material come into mutually abrading contact during agitation (e.g., shaking) of the plant material/lysis buffer mixture. The particulate matter is generally spherical and constructed of suitable material (e.g., stainless steel). Since generally spherical, the particulate matter can be considered to be in the form of a “BB.”

After a suitable period of agitation of the plant material/lysis buffer mixture, the resulting mixture generally comprises a lysed plant material mixture including a solids fraction and a supernatant comprising nucleic acid to be recovered. The lysed plant material is then treated for purposes of separating the solids fraction and supernatant. This treatment generally comprises centrifuging the samples (i.e., the multi-well plate) under suitable conditions. Typically, the samples are subjected to treatment by centrifuging at from about 2500 to about 3500 revolutions per minute (rpm) for from about 5 to about 10 minutes.

Prior to agitation of the lysis buffer/plant material mixture, the mixture may be subjected to an incubation period. Generally, any incubation period proceeds for at least about 5 minutes, at least about 10 minutes, or at least about 15 minutes. During the incubation period, the mixture may be subjected to temperatures of room temperature, or even higher. For example, the mixture may be subjected to temperatures of up to about 25° C., up to about 35° C., or up to about 45° C. The precise combination of time/temperature incubation conditions is not narrowly critical, however, in various embodiments, the incubation proceeds for a up to about 15 minutes while the mixture is subjected to a temperature of from about 20° C. to about 30° C. (e.g., about 25° C.).

Separation of the lysed plant material mixture (e.g., by centrifuging) forms a mixture including a nucleic acid supernatant that is then recovered from the lysed plant material mixture. The nucleic acid is then subjected to analysis by any method known in the art, including but not limited to those listed below.

Advantageously in accordance with the present invention, the lysis buffer provides for more rapid recovery of DNA. It is also currently believed that the lysis buffer provides DNA samples that indicate relatively high DNA yield and high sample purity.

These results are provided by the efficient and effective separation of DNA from the plant material provided by the components of the lysis buffer. Advantageously, these results are also combined along with processing advantages attendant the improved lysis buffer. Processing for separation and recovery of DNA utilizing conventional buffer typically includes filtration of the plant material/lysis buffer prior to subsequent treatment (e.g., agitation and centrifugation) for removal of various components of the mixture (e.g., cellular debris) that may interfere with DNA separation and recovery. Although such methods have proven effective, the filtration step often results in loss of DNA for separation and recovery near the outset of the separation/recovery process and also increases the expense associated with recovering each sample. In accordance with the present invention, it has been discovered that the lysis buffer may be utilized in a DNA separation/recovery process that does not require filtration of the plant material/lysis buffer mixture prior to processing for separation and recovery of DNA. Since DNA is not lost by filtration, a relatively high proportion (if not substantially all) of the DNA present in the plant material remains during and throughout the separation/recovery process. That is, each mixture and composition yielded during the separation/recovery process (e.g., the lysed plant material mixture and nucleic acid supernatant) includes a relatively high proportion of the DNA content of the starting plant material. For example, in various embodiments, the DNA content of the lysed plant material mixture and/or the nucleic acid supernatant is at least about 50%, at least about 60%, at least about 70%, at least about 80%, at least about 90%, at least about 95%, or at least about 99% of the DNA present in the plant material prior to lysing the plant material. Typically, higher yields are achieved in connection with bulk samples vs. leaf and chip samples, while higher yields are also typically achieved in connection with leaf samples vs. chip samples. In addition, eliminating the filtration step also provides a method in which the cost per sample recovered for analysis is reduced as compared to conventional methods that include the filtration step.

IV. Nucleic Acid Analysis

The nucleic acid of the supernatant can be utilized for DNA analysis in connection with any suitable method known in the art. These include marker-assisted breeding studies. These also include genotyping, DNA sequencing, allele specific oligonucleotide probes, hydridization, and single nucleotide polymorphism (SNP) detection. For example, the recovered DNA can be subjected to genotyping by a method selected from the group consisting of polymerase chain reaction (PCR), restriction fragment polymorphism ID of genomic DNA, random amplified polymorphic detection of DNA, and amplified fragment length polymorphism detection.

For PCR analysis, the samples are generally diluted prior to analysis. For example, in the case of leaf plant material, typically the sample is diluted at a ratio of (sample:aqueous medium) from about 1:10 to about 1:100. For chip samples, typically the sample is diluted at a ratio of from about 1:10 to about 1:50. By way of further example, for bulk samples (e.g., for plant material from corn, soy, cotton, canola, and cucumber), the sample is typically diluted at a ratio of from about 1:50 to about 1:1000.

In addition to DNA analysis generally, DNA recovered utilizing the present lysis buffer is suitable for microfluidic DNA analysis conducted generally in accordance with methods known in the art. In various particular embodiments, the recovered DNA is subjected to microfluidic PCR analysis.

Having described the invention in detail, it will be apparent that modifications and variations are possible without departing from the scope of the invention defined in the appended claims.

EXAMPLES

The following non-limiting examples are provided to further illustrate the present invention.

Example 1

The following example details use of an extraction buffer of the present invention for extraction of DNA from plant material derived from corn.

The extraction buffer was prepared from a TSES OMNIPUR buffer commercially available from EMD Millipore and having the following composition: 200 millimoles (mM) tromethamine (Tris); 250 mM sodium chloride (NaCl); 25 mM ethylenediamine tetraacetic acid (EDTA); and 0.5 wt % sodium dodecyl sulfate (SDS) in deionized water.

Volumes of the TSES were utilized on an as-needed basis and to these volumes were added the following components to provide the listed concentrations of each of these components: 125 mM NaOH; an additional 0.5 wt % SDS to provide a total concentration of 1 wt %; 1% v/v glycerol; and 1% w/v polyvinylpyrrolidone with an average molecular weight of 10,000 (PVP-10) commercially available from Sigma-Aldrich.

The following protocol was followed for the DNA extraction. Plant material samples were added to each plate of a 96-well plate constructed of polypropylene. To each well of the plate was added a spherical stainless steel pellet (or "BB") along with 50 microliters (uL) of the lysis buffer and 750 uL of water. The chip plate was sealed using a capmat (a rubber or plastic sheet with 96 raised knobs which fit into a corresponding well on the 96-well plate). The thus configured chip plate was shaken for approximately 12 minutes using a commercially available Harbil 5 gallon paint shaker (Model #5GHD). The chip plate was then spun for approximately 5 minutes using a commercially available centrifuge operated at 3500 revolutions per minute (RPM). The supernatant is then removed from each of the wells and subjected to micro-fluidic PCR (polymerase chain reaction) testing to identify the presence of certain markers, or single nucletotide polymorphisms (SNPs) in the plant material samples analyzed. The conditions of the micro-fluidic PCR are as follows:

| 1.3 uL Rxn | | |
|---|---|---|
| Reaction Mix | Stock Conc | uLs |
| Mastermix (ABI) | 2X | 0.65 |
| ABI Assay | 16 uM | 0.02 |
| $H_20$ | | 0.63 |
| DNA | variable | 1 |

Cycling Conditions

| | | |
|---|---|---|
| 95 | 10 min | |
| 92 | 15 sec | 40 cycles |
| 60 | 1 min | |
| 10 | infinity | |

The above protocol is generally displayed graphically in FIG. 1.

Similar analyses were conducted using a conventional lysis buffer (e.g., the OMNIPUR TSES buffer described above) and following the method detailed in Dellaporta et al. Plant Molecular Biology Reporter, Vol. 1, No. 4 (1983). As compared to the protocol described above for the testing conducted using the lysis buffer of the present invention, this protocol includes a filtration step of the spun samples between the centrifuge and supernatant recovery steps.

PCR analysis was conducted to determine the effectiveness of the lysis buffer and protocol of the present invention. PCR analysis was also conducted to determine the relative effectiveness of the present lysis buffer/protocol as compared to the Dellaporta et al. method. The Dellaporta et al.

method is commonly recognized as a standard in the art and, therefore, is a suitable comparator for the present lysis buffer/protocol.

PCR analysis was conducted to determine the presence of the following markers in the plant material:

(1) Q-NC0009867
(2) Q-NC0015344
(3) Q-NC0199537
(4) Q-NCO201917
(5) Q-NCD591227
(6) Q-NCMON8801
(7) Q-NCMON89034
(8) Q-NCTC1507

Sequence listings for Markers (1)-4) are set forth below.

PCR analysis generated cluster graphs for each of the well-plates. 160 plots were tested for each of the present lysis buffer/protocol and Dellaporta protocol and subjected to PCR analysis. Each plate corresponded to a specific marker and a specific seed type.

Main effects plots were generated for the PCR result for each of the plates and these results were analyzed by a trained observer to determine the quality of the results. In particular, these results were analyzed to determine signal strength, clustering of homozygous and heterozygous traits, and the presence of the homozygous and heterozygous trait clusters near the x or y axis of the main effects plot. Following is a representative main effects plot.

The trained observer rated the results using the following scale:

5—Excellent (high signal strength, tight clusters, clusters near the axes, greater than 50% of the standard controls matching/amplifying, z at origin) The corn standard controls are as follows:

S1=13_B73/MO17
S2=13_LH82/B73
S3=13_LH82/MO17
S4=B73HT
S5=LH82
S6=MO17HT

4—Very good (high signal strength, tight separated clusters, very few outliers, greater than 50% of the standard controls matching/amplifying, z not necessarily at origin)

3—Good (not necessarily a high signal strength, clusters separated but not necessarily tight, genotypes still clear, more outliers/ambiguous/missing samples (less than 5%), greater than 50% of the standard controls matching amplifying, z not necessarily at origin)

2—Fair (questionable genotypes, greater than 5% outliers/ambiguous/missing data, can faintly define borders around clusters)

1—Poor (rainbow of data, cannot distinguish genotypes, clusters not defined)

0—Failure

Results for 160 well plates analyzed by the present SNAP method and the Dellaporta (DP) method were compiled into:

1) Interaction plots
2) Time Series plots
3) Main Effects plots

These results are shown below. As shown on the time series plot, the results for the SNAP process and the DP process exhibited similar variability. The interaction plot indicates variability between the DP and SNAP process based on the particular marker being tested for. For certain markers, the overall rating compiled for the DP process was higher than that compiled for the SNAP process, and vice versa. However, overall these results indicate overall sufficient performance for both the DP process and also the SNAP process. The Main Effects plot provides the following data: (1) overall ratings for each marker and (2) a comparison of the combined ratings across all markers tested for the DP and SNAP process. In combination with the Interaction Plot, the overall marker ratings (1) of the main effects plot indicate that similar performance of the DP and SNAP process. For example, the overall rating for marker Q-NC0009867 was 3.0. The rating for this marker for the DP process was 3.5 while the rating for the SNAP process was 2.5. Thus, the overall rating of 3.0 for marker Q-NC0009867 was not provided by a significant weighting of the results for the either the DP or SNAP process. Similar results were observed for the other markers tested. In addition, the "Process" results on the Main Effects plot indicate an essentially equivalent rating of 2 for both the DP and SNAP processes across all markers.

Time Series and Interaction Plots

Figure 2:
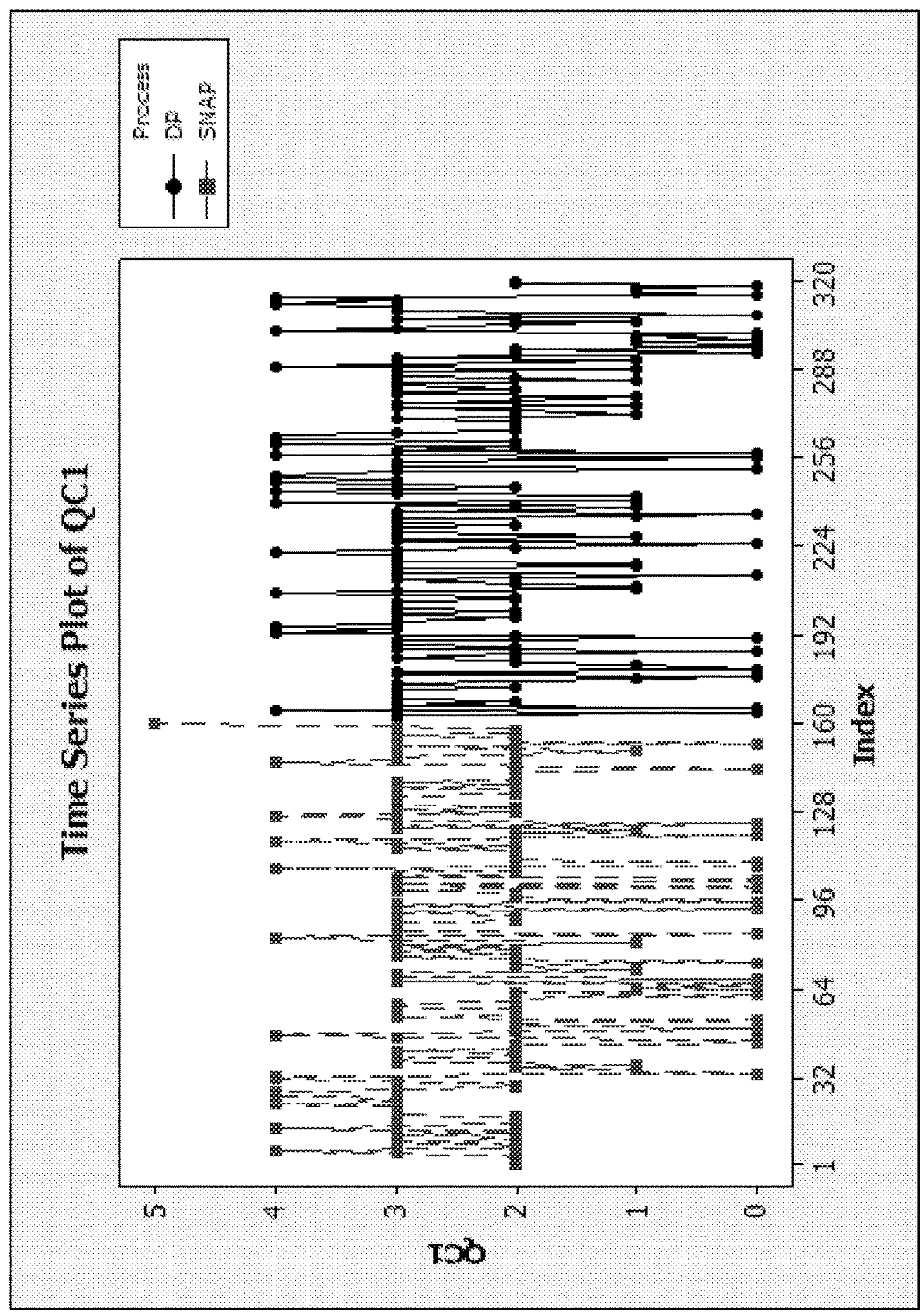
FIG. 2 is a Time Series Plot generated as described in Example 1.

The Time Series Plot shown in FIG. 2 is the order of the final p-plates after PCR. Based on the QC members subjective score (the ordinal scale) they were plotted. All the effects (markers, PCR, chipping) are considered noise here. Normal behavior is expected. A trend within the process (Red/left is SNAP and Black/right is DP) would show special causes which could be something related to the something else in the process which was not being tested here.

Figure 3:
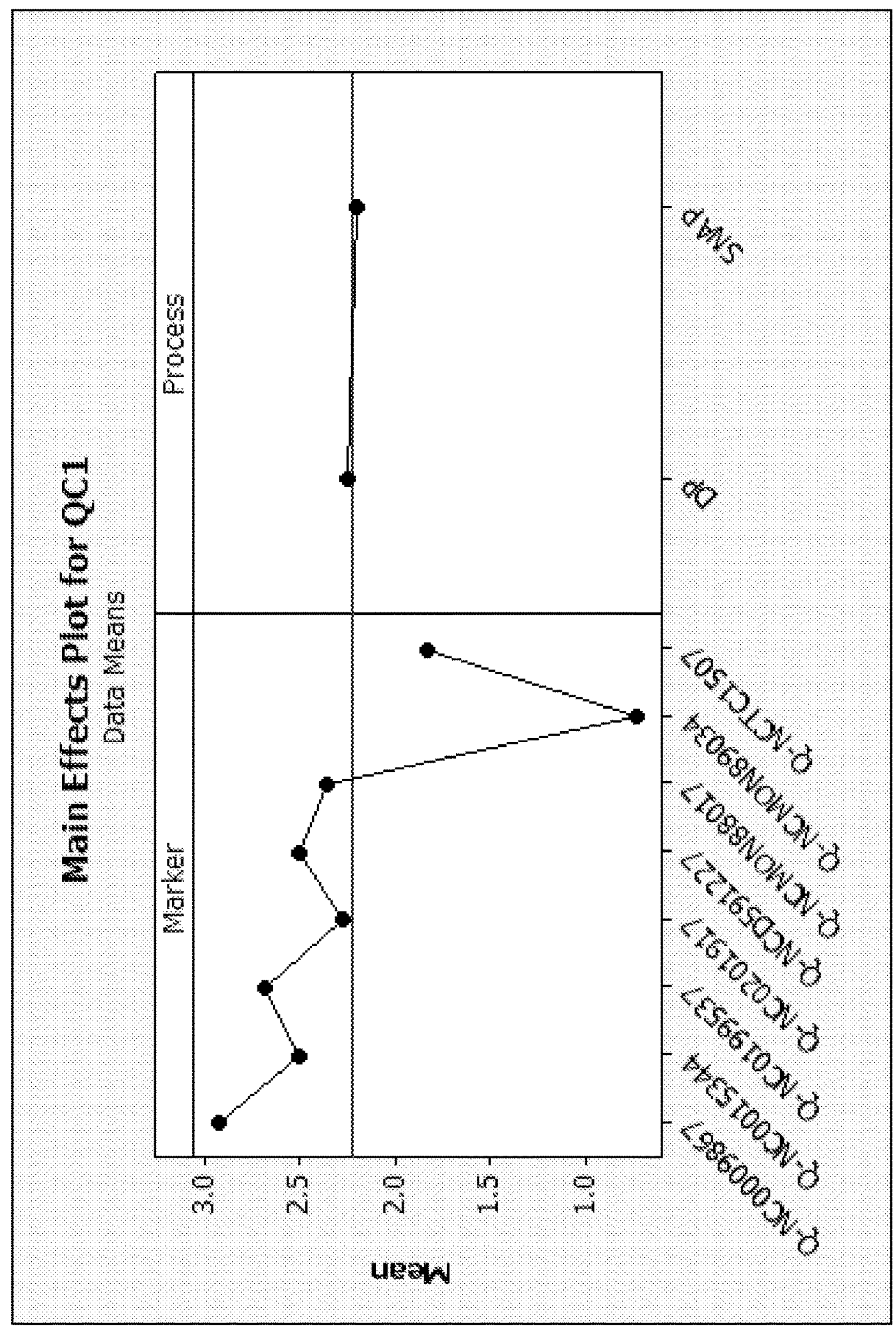
FIG. 3 is a Main Effects Plot generated as described in Example 1.

Main Effects Plots, such as FIG. 3, are used to identify the impact of concerned factors. They take all the variables within the factors and achieve a mean value which is plotted. For example, the right side of the plot in FIG. 3 has 2 data points. DP data point is the average of all the 160 points and SNAP is the average of all 160 points. Nothing else is considered here. The plot on the left side of FIG. 3 is for the marker. It does not consider the process of extraction—just the behavior of the markers overall. Statistically, markers were significant but the extraction process was not.

Figure 4:
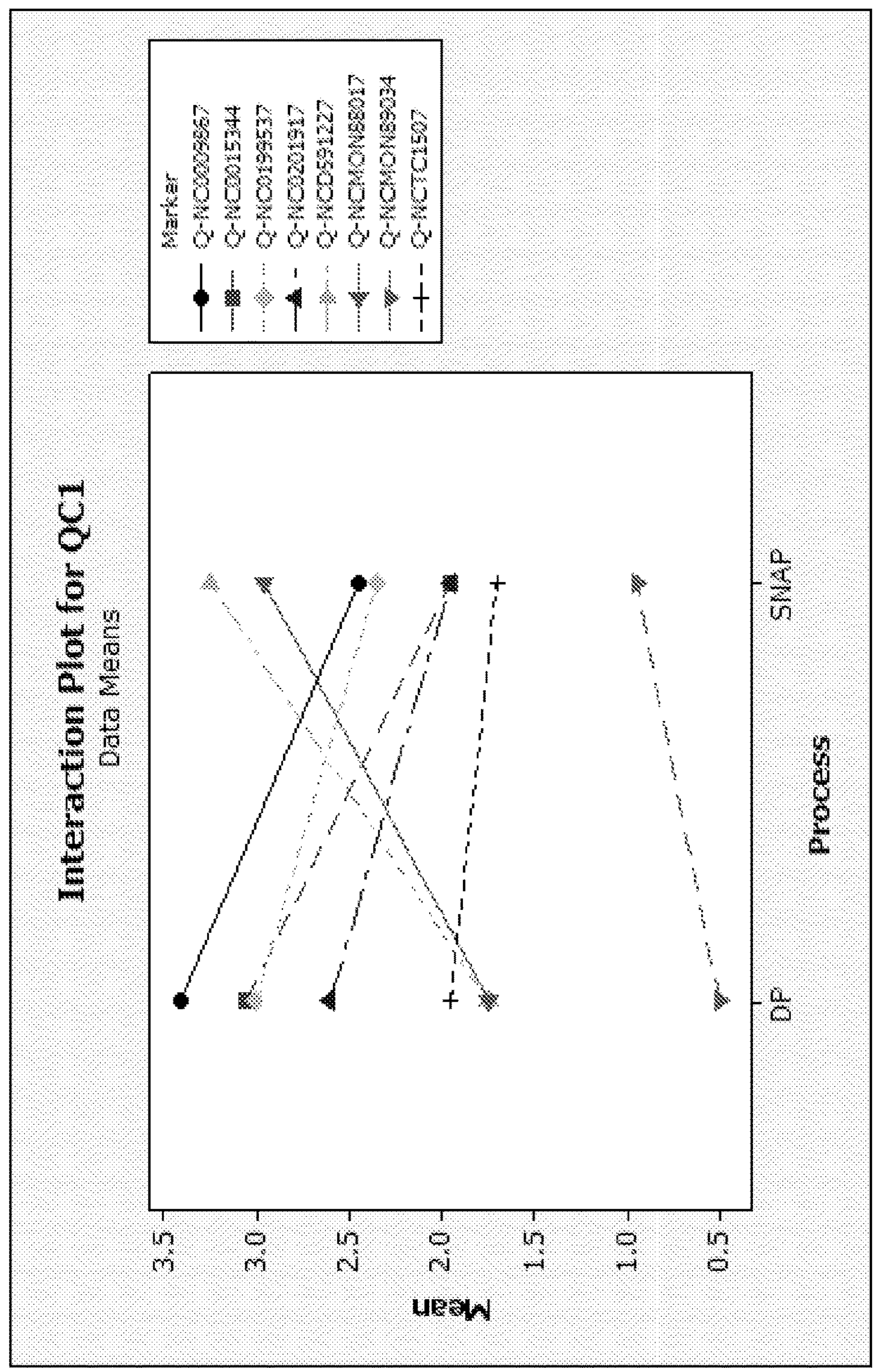
FIG. 4 is an Interaction Plot generated as described in Example 1.

Interaction Plots, such as FIG. 4, are utilized to identify the special relation between the markers and the extraction process. As seen in FIG. 4, some markers work well with the SNAP process compared to DP while others work better with DP. This is expected considering the marker effect in the process. Each data point on the plot takes the average of all the values with the specific extraction method and marker. There were multiple replications in the test so there were more than one combination of the extraction process and marker.

In addition to the above-described time series and interaction plots, a concordance study was conducted. This study was to identify the proportions of markers that were present in samples analyzed by the DP method and the SNAP method. In particular, this study identified the proportion of identical "calls" (i.e., identified markers or SNPs) that were identified in samples identified by both the DP and SNAP processes.

A missing call from either process is removed from the calculation for concordance. Concordance depends on the markers too and this information along with the % recovery needs to be forwarded to the breeder.

Results of the following analyses were used for the concordance study: DP analysis of leaf samples, SNAP analysis of leaf samples, and SNAP analysis of chip samples. In particular, the following comparisons were made and the results are summarized in the table below:

1) DP leaf sample analysis to SNAP leaf sample analysis
2) DP leaf sample analysis to SNAP chip sample analysis
3) SNAP leaf sample analysis to SNAP chip sample analysis Following is a key for the results shown in the below table:

(a) Missing Left—missing calls from the left side of the title (e.g., DP leaf sample analysis of SNAP leaf sample analysis)
(b) Missing Right—missing calls from the right side of the title (e.g., SNAP leaf sample analysis or SNAP chip sample analysis)

(c) Adjacent—Assuming left side is right; the calls from the right side have jumped from homozygous (+ or −) to heterozygous, or vice versa (d) Flipped—Assuming left side is right; the calls from the right side have jumped from homozygous (+) to homozygous (−), or vice versa

| | L DP (left) - L SNAP (right) | | L DP (left)- CHIP (right) | | L SNAP (left) - CHIP (right) | |
|---|---|---|---|---|---|---|
| Missing Left | 393 | 3.12% | 393 | 3.12% | 1763 | 13.99% |
| Missing Right | 1626 | 12.90% | 653 | 5.18% | 570 | 4.52% |
| Adjacent | 152 | 1.21% | 1888 | 14.98% | 1652 | 13.10% |
| Flipped | 0 | 0.00% | 58 | 0.46% | 59 | 0.47% |
| Matches | 10435 | 82.78% | 9614 | 76.27% | 8562 | 67.92% |
| Total | 12606 | | 12606 | | 12606 | |
| Concor-dance | | 98.79% | | 84.56% | | 86.43% |

Figure 5:
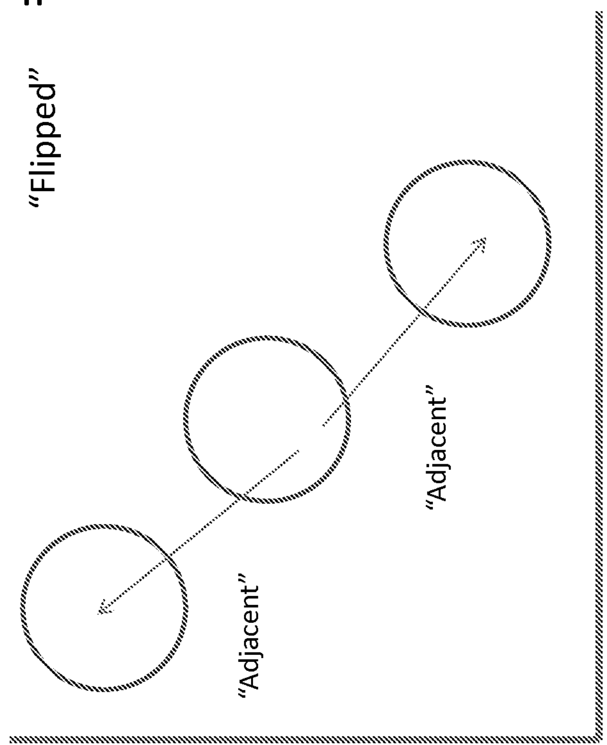
FIG. 5 provides a graphical representation of concordance data gathered as described in Example 1.

Following is calculation of concordance taking into account adjacent and flipped calls. FIG. 5 includes a graphical representation.

Concordance=1−(adjacent+flipped)/total

Sequence Listings: Markers (1)-(4)

Example 2

The following example describes the results of DNA analysis (genotyping) for bulk canola samples comparing the SNAP protocol to the Dellaporta protocol.

An extraction protocol as described above in Example 1 was conducted for bulk canola seeds (more than one seed) to evaluate the performance of the SNAP protocol and the Dellaporta protocol. The marker evaluated for testing both protocols was NR00LLR1A.

For SNAP protocol testing, the bulk sample consisted of five seeds (5). After extraction and prior to DNA analysis (genotyping), the sample was diluted (1:1000). Results showed distinct clustering enabling successful genotypic calls with a fail rate of 1.59% for the marker evaluated (NR00LLR1A).

For the Dellaporta protocol testing, the bulk sample consisted of ten seeds (10). After extraction and prior to DNA analysis (genotyping), the sample was diluted (1:1000). The results failed. Clustering was not distinct; genotypic calls could not be made. Failure rate was greater than 10% for the marker evaluated (NR00LLR1A). These results were consistent with testing of additional markers.

When introducing elements of the present invention or the preferred embodiments(s) thereof, the articles “a”, “an”, “the” and “said” are intended to mean that there are one or

| Marker | SEQ ID NO: | Sequence |
|---|---|---|
| Q-NC0009867 | 1 | ATAACTACATATAATTTCTATTGTTATCTTTNGGGGGTACCATGTGCACTAACACATACTGCATTCGTGGA<br>TCTGTTTATTATATTGTGCAGGTTAAGAAAAAGTTGGTGAATCTGGGTCATGCACAGAGGTACGTCGTGA<br>TTTGCTAATNTGTNATTTTAAGAAAAGGGCAGACCCGGTATCGAAGGCTCCCATGTGAGTGGGGTTTGG<br>GGAGAGAAACCGAGGCAAGTCTTCCTCCACAAATGTGGAGAGGCTGCTTCGAATCAGCGACTGGTGCCT<br>CAGTGAGACAGCTCTCACCACCGCACCAGGCGTGCTCTTCGTTTACTAATCTGCTATTTAATAAAGCACAA<br>TGAACAGACTACCATCTTTATGTTCAAATCGAAAATAGTGAGGAATCACTTCATTTGCTGATTTTAAGTTC<br>CTGGCCTAATCTAAATGTTAGTTTTTTAAGGCTTTGAATTCNANNNNNNNATTNNGNNNNNTCTGAAAA<br>ATGTCATTTTTTATTCTTATATGGAAGTTNNNAAATATGCAAATATGACNAACNNNNNNNNNNNNNNN<br>NNNNNNNNCNNNTATGATCTANNNNNNNNNNNNNNNNNNNNNNNNNNNNNNNNNTNNNNNNNNNN<br>NNNNNNNNNNNNNTG |
| Q-NC0015344 | 2 | TCTACTGGTGTTCAATTGGTTTCTAACATATGAAAAGATGTGCCAGCCAAAATTCTGTTTTGATCTGTTAG<br>ATGATGTATACATGCCCATGTGATATTGGAGTTACATATGGCTAATATAAAAANGACACCTGAACCTTAG<br>GCAAGATGAAAGGCAGCTTTCTTCTTGTTTCCATTNATTGTTCCTGTTTTGACTCATTTATGCTGAAATTGC<br>TGATGCTATTTACTTCTTTTCTGACCATAAGGATGGGGGTTGCAACTTCTTTGAGTGGTGCGATGCTCCAT<br>CTCCCGCCCCTGCCAATGCACGAAATAACATGGTTGTACACTCAGAGACATCAGCAACAGATATGCTTTG<br>CCCATGCAGTGCTGGAACTTGCTTAATTCTCACCACAAAGACAGGGAAAAATGTTGGGAGGCAATTCTTT<br>TGCTGCCCATTAAATCAGGTAAACTCAGGATTCACCAATGTTACCTGAATTCATGACATTTTGCCGTACCA<br>NATAGCGGCCTATACTGGTTTGTTTTTCTGGAAGAACTTGGCCCCTTTTTATCTGACACAACTTGTTTAATT<br>ATAACATTGAACATCTGCAACCCTACTCNTNNNTGAATTTGAGTANTCAACATTTGTGGNATTTTGAACN<br>NGNNTNATTATAACATTGAACATCNGCNNC |
| Q-NC0199537 | 3 | GTCGATCCGTTCCTTCAAAATTGATTCCAATCGGATTGCTCCCTCAAAGTTGCTCTTCAAATTCTAGGGAA<br>TAAATGCTATAGTTGGCGCACGCGCAGTCGATATGGGAATTTTGACCACCCCTCAACTGCATTGGATGGT<br>CCGGAGCAAAAACAAAGGTGTCATGGCTTCCGAGTCAGATTATTTTAGGCAGCTTATTGGATCGTTCAGG<br>TTATTTTCTAGTCATTGTCCTGCTGCTTTTAGTCTCCCACGAACTACTATAGTGTCTTTGATGATGAGTTTCT<br>AGCATCAAATTTCACCAGGCGTATGTTGGAATTAGTGCCAAAAGGTAAAGGTGGGGATGAGGTTGCCAA<br>GAAACTTATTGTCGATGGAGCAAATGGCATTGGTGGGGTGAAGCTCGAACAAATAAAGGTGGAGCTTTC<br>AGGCATAGATATTAGTGTGAGGAATTCGGGCAAGGAAGGAGAAGGGATACTAAATCACATGTGTGGCG<br>CAGACTTTGTTCAAAAGGAGCGAGTTACTCCACATGGATTTAACCCTGAAGATGTT |
| Q-NC0201917 | 4 | CTATGGAAGCTCCCAGTACGGTCCACCACTCTGTCAGGTGAGAAGAAGCTTAATTATATTGATTAAATAT<br>AACAACTAACTGGAGCAAGACTAAAGGAAATAAAACATGTTTTTTTTGTGGGAAATCCCCTACATTTTCTA<br>ATTTCTACTCATGTAAAACTAGCTACTGCAGGTTGTTGTCAATGCCATCACTTGAATTTAGCTAGAGAGAT<br>TTATTTATTTATTTATTTCTTACCAGCACTGTCGAACCTCTGGCTGCCAGGGCGACAGTGTCAGCACAGGA<br>CACCGTCTGCGGACATGCTTCCTCGAGTGCAGCTTTGATCTCGTCTATGACCTCAAACCCCCTAATGGAAT<br>CCTTGTTGGGGATAGCGTTTTTCTCGCTCACGACTTCCTCAGCGTCATCCAAAAGAACCGACGCATCGCA<br>GCCCTGCGATAGTGCGATTAGTTTCATCGCATGAACCACGGCCGGGACAAAAGAGACGATTGACCAAAT<br>AGAGAACATGAGACCGTAGTGCTGCTAACCTGGACAAAGCAGTCATGGAACAGGAGCCTGAGAAGGGA<br>GGCAGCTACCCGTGGTTCCTTCGCGATAGCCTTCTTCAGTATGGGCGCCACCGTCTCGTCAGCTTGCGGG<br>CATGTCAACCTGTAGTAGTCTGTAGAAAGACCTGGGATTGGAGTACTTCCA |

more of the elements. The terms “comprising”, “including” and “having” are intended to be inclusive and mean that there may be additional elements other than the listed elements.

In view of the above, it will be seen that the several objects of the invention are achieved and other advantageous results attained.

As various changes could be made in the above compositions and methods without departing from the scope of the invention, it is intended that all matter contained in the above description and herein shall be interpreted as illustrative and not in a limiting sense.

What is claimed is:

1. A cell lysis buffer composition, the composition comprising:

(a) a buffering component selected from the group consisting of tris(hydroxymethyl)aminomethane, 4-(2-hydroxyethyl)-1-piperazineethanesulfonic acid, 3-(N-morpholino)propanesulfonic acid, sodium dihydrogen phosphate, disodium hydrogen phosphate, and combinations thereof, wherein the buffering component is present in the composition at a concentration of from 100 mM to 300 mM;

(b) a mineral salt selected from the group consisting of sodium chloride, potassium chloride, diammonium sulfate, and combinations thereof, wherein the mineral salt is present in the composition at a concentration of from 150 mM to 350 mM;

(c) a metal chelating agent selected from the group consisting of ethylenediaminetetraacetic acid, ethylene glycol tetraacetic acid, and combinations thereof, wherein the metal chelating agent is present in the composition at a concentration of from 10 mM to 50 mM;

(d) a surfactant selected from the group consisting of sodium dodecyl sulfate, nonyl phenoxypolyoxylethanol, polyethylene glycol p-(1,1,3,3-tetramethylbutyl)-phenyl ether, polyoxyethylene (20) sorbitan monooleate, and combinations thereof, wherein the surfactant is present in the composition at a concentration of from 0.5 wt. % to 1.5 wt. %; and (e) an alkali metal hydroxide comprising sodium hydroxide, potassium hydroxide, and combinations thereof, wherein the alkali metal hydroxide is present in the composition at a concentration of at least 75 mM, the composition further comprising one or more of the following components:

(A) a precipitant selected from the group consisting of glycerol, dimethyl sulfoxide, acetonitrile, bovine serum albumin, proteinase K, acetate salts, and combinations thereof; and/or (B) a water-soluble polymer comprising polyvinylpyrrolidone.

2. The composition of claim 1, the composition comprising sodium hydroxide at a concentration of from 100 mM to 150 mM.

3. The composition of claim 1, wherein the precipitant comprises glycerol.

4. The composition of claim 3, wherein glycerol is present at a concentration (v/v) of from 0.25 to 5.0%.

5. The composition of claim 3 wherein the surfactant comprises sodium dodecyl sulfate.

6. The composition of claim 3 wherein the alkali metal hydroxide comprises sodium hydroxide.

7. The composition of claim 3 wherein the buffering component comprises tris(hydroxymethyl)aminomethane.

8. The composition of claim 1 wherein the buffering component is selected from the group consisting of tris (hydroxymethyl)aminomethane, 3-(N-morpholino)propanesulfonic acid, sodium dihydrogen phosphate, disodium hydrogen phosphate, and combinations thereof.

9. The composition of claim 1 wherein the mineral salt is selected from the group consisting of potassium chloride, diammonium sulfate, and combinations thereof.

10. The composition of claim 1 wherein the metal chelating agent is ethylene glycol tetraacetic acid.

11. The composition of claim 1 wherein the surfactant is selected from the group consisting of sodium dodecyl sulfate, polyethylene glycol p-(1,1,3,3-tetramethylbutyl)-phenyl ether, polyoxyethylene (20) sorbitan monooleate, and combinations thereof.

12. A kit for analysis of DNA recovered from plant material, the kit comprising a composition as defined in claim 1.

13. A method for the isolation of nucleic acid from plant material, the method comprising:

combining the plant material and a cell lysis buffer composition as defined in claim 1, thereby forming a plant material/lysis buffer mixture;

agitating the plant material/lysis buffer mixture, thereby lysing the plant material and forming a lysed plant material mixture;

separating the lysed plant material mixture into a mixture comprising a solids fraction comprising plant material and a supernatant comprising nucleic acid; and recovering the nucleic acid supernatant from the lysed plant material mixture.

* * * * *